United States Patent [19]

Friedland

[11] Patent Number: 5,171,252

[45] Date of Patent: Dec. 15, 1992

[54] SURGICAL FASTENING CLIP FORMED OF A SHAPE MEMORY ALLOY, A METHOD OF MAKING SUCH A CLIP AND A METHOD OF USING SUCH A CLIP

[76] Inventor: Thomas W. Friedland, 2132 Dellesta Dr., Bellingham, Wash. 98226

[21] Appl. No.: 650,869

[22] Filed: Feb. 5, 1991

[51] Int. Cl.⁵ .............................................. A61B 17/00
[52] U.S. Cl. ................... 606/151; 606/157; 606/221; 227/902
[58] Field of Search ............ 606/158, 157, 151; 24/543, 545, 556

[56] References Cited

U.S. PATENT DOCUMENTS

| | | |
|---|---|---|
| 3,363,628 | 1/1968 | Wood . |
| 3,786,806 | 1/1974 | Johnson et al. . |
| 4,037,324 | 7/1977 | Andreasen . |
| 4,170,990 | 10/1979 | Baumgart et al. . |
| 4,233,690 | 11/1980 | Akins . |
| 4,260,375 | 4/1981 | Wallshein ............................ 433/11 |
| 4,414,721 | 11/1983 | Hufnagel ............................ 606/142 |
| 4,485,816 | 12/1984 | Krumme . |
| 4,490,112 | 12/1984 | Tanaka et al. . |
| 4,512,338 | 4/1985 | Balko et al. . |
| 4,556,050 | 12/1985 | Hodgson et al. . |
| 4,665,906 | 5/1987 | Jervis ............................ 606/78 |
| 4,696,396 | 9/1987 | Samuels . |
| 4,707,148 | 11/1987 | Richmond ............................ 374/208 |
| 4,734,543 | 3/1988 | Nolf ............................ 174/88 R |
| 4,805,618 | 2/1989 | Ueda et al. ............................ 128/831 |
| 4,834,096 | 5/1989 | Oh et al. . |
| 4,844,066 | 7/1989 | Stein . |
| 4,887,335 | 12/1989 | Folkmar ............................ 24/543 |
| 5,026,382 | 6/1991 | Peiffer ............................ 606/157 |

Primary Examiner—Stephen C. Pellegrino
Assistant Examiner—Jeffrey A. Schmidt
Attorney, Agent, or Firm—Bachman & LaPointe

[57] ABSTRACT

A surgical fastening clip of a shape memory alloy which applies a first clamping force to a site when the alloy is in its martensitic condition and a second clamping force to the site when the alloy heats due to surrounding tissue such that the alloy transforms to its austenitic condition. The second clamping force is greater than the first clamping force and prevents the clip from slipping or falling off the clamped site due to shrinkage or movement of the site. For instance, the site could be a blood vessel which becomes thinner due to the compressive force of the clip and shrinks, but the clip maintains a clamping force on the blood vessel due to the shape memory effect of the alloy. A method of using a surgical fastening clip formed of a shape memory alloy by placing opposed legs of the clip around a site, deforming the legs to a closed configuration and heating the clip by the natural surroundings to cause further closing of the legs and thereby increasing the clamping force. A method of making a clip formed of a shape memory alloy by deforming the clip to a closed configuration, heating to the austenitic state, setting the memory of the alloy, cooling to the martensitic state, and deforming the clip to an open configuration.

28 Claims, 4 Drawing Sheets

SURGICAL FASTENING CLIP FORMED OF A SHAPE MEMORY ALLOY, A METHOD OF MAKING SUCH A CLIP AND A METHOD OF USING SUCH A CLIP

BACKGROUND OF THE INVENTION

1. Field of the Invention

The present invention relates to an improved surgical fastening clip, a method for the production thereof and a method of using the surgical fastening clip. In particular, the surgical fastening clip is formed of a shape memory alloy which provides a clamping force even when the object being clamped shrinks, thins out or moves. The device may change shape to project "teeth" into the object to further enhance its grasping and non-slip capabilities.

2. Description of the Prior Art

Various medical devices formed of shape memory alloys are known in the art. For instance, U.S. Pat. No. 4,170,990 ("Baumgart") discloses a method for implanting and subsequently removing mechanical implants of an alloy which exhibits a memory effect, the implant being removed by cooling it to a temperature below the temperature which actuates the memory effect. Baumgart discloses that such implants can include nails, wires, sutures, clamps, clips, sleeves, rings, discs, pins or tubes. Baumgart further discloses that separation in living tissue can be fixed by rotating, compressing, bending or twisting of the implant by utilization of the memory effect. Accordingly, changes in shape when the implant is used result solely from temperature changes. Baumgart does not disclose a surgical fastening clip of a shape memory alloy which is mechanically deformed such that the legs of the clip clamp an object therebetween.

U.S. Pat. No. 4,665,906 ("Jervis") discloses medical devices of shape memory alloys which exhibit stress-induced martensite at body temperature. In particular, a shape memory alloy at a temperature between $M_s$ and $M_d$ but below $A_s$ is initially, austenitic and application of a stress exceeding $\sigma_M$ forms stress-induced martensite until the alloy becomes fully martensitic, after which application of further stress causes the alloy to deform elastically and then plastically. If the stress-induced martensite is not plastically deformed, release of the stress allows the martensite to recover elastically so as to have zero residual stress but a non-zero residual strain. Heating the alloy above $A_s$ results in reversion to austenite, and if the alloy is unrestrained, the original shape will be recovered. If not, it will be recovered to the extent permitted by the restraint. Upon cooling to the temperature at which the alloy was deformed (or a temperature at which stress-induced martensite is seen), the stress produced by the alloy will be constant. The alloy can thus provide a constant force over a strain range of about 5%.

Alternatively, at a temperature between $M_s$ and $M_d$ but above $A_s$, upon application of stress the alloy deforms elastically and when the stress exceeds $\sigma_m$ forms stress-induced martensite after which the martensite is deformed, as described above. The unloading behavior is different from that described above in that the alloy recovers elastically at first until an essentially constant critical stress $\sigma_A$ is reached at which point the alloy reverts to austenite without requiring a change in temperature. Then, if the stress is removed from the reverted austenite it recovers elastically. The alloy can thus provide a constant force over an effective working range of about 5%.

Jervis discloses a shape memory alloy ring for holding a sewing cuff to the body of an artificial heart valve. Jervis discloses that such a ring had previously been described as being made in the austenitic state, cooled to the martensitic state, deformed, placed around the valve body and heated to cause reversion to austenite. According to Jervis' invention, the ring is made in the austenitic state, cooled to the martensite phase, expanded, placed around the valve body, heated above $A_f$ and cooled, whereby a constant force is applied to the valve body. Jervis also discloses bone staples, clips, etc. made of a shape memory alloy. In particular, Jervis discloses a staple made of an alloy below $A_s$ which is for holding fragments of bone together, the staples being placed in the martensitic state, heated to the austenitic state and cooled to body temperature to achieve constant force. Above $A_s$, the staple is held in the deformed position by a moderate force and then released after insertion to provide an accurately-known force. This allows easier removal by deformation which forms stress-induced martensite.

U.S. Pat. No. 4,556,050 ("Hodgson") discloses an artificial sphincter which includes an implantable clamp for selectively pinching closed or opening a vessel in a living body. The clamp includes a spring member and a shape memory member. One of the opening and closing operations is effected by deforming the shape memory member from the memory configuration, and the other of the operations is effected by heat recovering the shape memory member to the memory configuration by heating above body temperatures. Heating is accomplished by means of an ac source via a coil in the shape memory member.

U.S. Pat. No. 4,485,816 ("Krumme") discloses a surgical staple which is formed into a desired closed position at a temperature above the transition temperature and then cooled below the transition temperature before deforming it into an open position, the resulting staple reverting to its closed position when it is subsequently reheated by means of an electrical power supply above the transition temperature, the transition temperature being in the range of 50°–80° C.

Other medical devices of shape memory alloys are disclosed in U.S. Pat. No. 3,786,806 ("Johnson") which discloses a plate formed of a shape memory alloy for drawing fractured bone ends together, U.S. Pat. No. 4,233,690 ("Akins") which discloses a prosthetic element of a shape memory alloy which can be used as a coupling element, U.S. Pat. No. 4,490,112 ("Tanaka") and U.S. Pat. No. 4,037,324 ("Andreasen") which disclose components of shape memory alloys having dental applications, and Soviet Union Publication No. 1,110,447 which discloses a compressing fixator of a shape memory alloy for use in healing bone fractures.

Various types of surgical clips are known in the art. For instance, U.S. Pat. No. 4,844,066 ("Stein"), U.S. Pat. No. 4,834,096 ("Oh"), U.S. Pat. No. 4,696,396 ("Samuels") and U.S. Pat. No. 3,363,628 ("Wood") disclose various types of surgical clips. Five manufacturers sell hemoclips in the United States; such manufacturers include Ethicon (Johnson & Johnson), Weck (Squibb), Richard Allen, Pilling (Japanese) and Auto Suture.

Surgical fastening clips (or hemoclips) are currently used in surgery to prevent bleeding by squeezing vessels and tissue. The clips are left in the body at the conclusion of the operation. Conventional clips are made of malleable stainless steel, titanium or tantalum and are squeezed together on the tissue by plier-like forceps. The metal clip is thus closed by plastic deformation. All of the commercially available clips will frequently slip off the tissue during or shortly after completion of surgery, thereby lessening their effectiveness and decreasing their use to situations wherein a slipping clip is not a vital problem.

The alternative to clipping is suture ligating which is more secure but takes much longer to do. There are many situations wherein all surgeons refuse to use surgical fastening clips because they are not secure enough, and many surgeons simply do not use the clips at all because of their unreliability.

All of the conventionally available clips have some "spring back" when they are squeezed together which then results in the two legs of the clip not lying in opposition but actually having some gap therebetween. Such clips also will not follow tissue as it shrinks in thickness; thus, with such clips there will not be a continuing squeezing force to keep the clip on the tissue. The present invention overcomes a major drawback of the existing clips—their unreliability.

SUMMARY OF THE INVENTION

According to the present invention, a surgical fastening clip is provided which can be applied in a manner similar to existing conventional clips. The clip of the invention, however, comprises a shape memory alloy which undergoes a shape memory effect when the alloy is heated into the austenitic state. In this state, the clip exerts a squeezing force on the tissue which will continue to close the clip and follow the tissue as it thins out.

The clip, according to the invention, can include interdigitating teeth along the arms and the end thereof that will dig into the tissue, thereby greatly increasing its resistance to slip and thus also making it far more secure. The clips of the invention will be more dependable and will be usable in more situations than the existing conventional clips. They can also be made in larger sizes and could replace surgical stapling devices.

In accordance with the invention, a surgical fastening clip is provided as a substantially U-shaped member of a shape memory alloy having a martensite transformation temperature below which the alloy transforms to its martensite state and an austenite transformation temperature above which the alloy transforms to its austenite state. The clip is deformable in its martensitic state from a closed configuration to an open configuration and recovers to the closed configuration when heated to transform the alloy to its austenitic state. The clip is open and capable of being deformed in its martensitic state so as to apply a first clamping force on an object and so as to apply a second clamping force on the object when the alloy is heated to transform it to its austenitic state, the second clamping force being greater than the first clamping force.

The clip will be squeezed onto the object tissue by a pliers-like device using plastic deformation of the metal of the clip in the manner in which existing clips are applied. As the clip then rises to body temperature, it passes through its shape memory transition temperature and attempts to return to the shape in its memory. This causes the two legs of the clip to attempt to move closer together, thus exerting an increased clamping force on the object. The clip may also change shape to form interdigitating corners or "teeth" that press down into the tissue, thus further enhancing its gripping power. The ends of the arms may also bend down into the tissue preventing the clip from slipping back off the tissue. If the clip forms a "zig-zag" shape, as one design may, the effective length of the arms will shorten and thereby bunch up the tissue, making it thicker and easier to grip.

A superior clamping, clipping or fastening device will lend itself to new applications in surgery. It will be possible to be used to connect together portions of intestine, arteries, veins, tendons or other tissues that are presently sutured together by sutures or stapling devices. Increased confidence of the clip as a surgical fastening clip will allow its use as a surgical fastening device for major (larger) arteries and veins where prudence prevents the existing clips from being used.

In accordance with another feature of the invention, a method of making the surgical fastening clip is provided. In particular, the method comprises: (i) providing the alloy in the form of an elongated member; (ii) forming the member into a clip having a substantially U-shaped configuration with two spaced-apart opposing legs extending in a longitudinal direction; (iii) deforming the clip such that the opposing legs are squeezed together in a closed configuration; (iv) heating the clip in the closed position such that the alloy transforms to its austenitic state; (v) cooling the clip such that the alloy transforms to its martensitic state; and (vi) deforming the clip such that the legs are moved away from each other from said closed configuration to an open configuration. The clip can be heat-treated in one or more steps during the process of making the clip. Step (iii) can further include forming at least one projection on at least one of the legs such that when the clip is in its closed configuration the projection extends through a plane extending between the legs, or step (iii) can include forming a plurality of projections on each of the legs such that when the clip is in its closed configuration the projections interengage. Alternatively, step (iii) can include forming each of the legs with at least one bend along a length thereof, and step (vi) can further include straightening each of the legs such that the legs are elongated in said longitudinal direction.

In accordance with another feature of the invention, a method of in vitro clamping of living tissue is provided. This method includes: (i) placing opposed legs of the surgical fastening clip of the invention which is in an open configuration around a site of living tissue; (ii) pressing the legs together to the closed configuration; and (iii) heating the clip such that the alloy transforms to its austenitic state and the legs are urged together due to the shape memory effect of the shape memory alloy. Step (ii) can be performed at an ambient temperature or at a temperature in the range of 20° to 25° C. Then the clip undergoes the shape memory effect by heating in step (iii) to a temperature of less than 37° C., such as 30° to 35°. Step (ii) can be performed with surgical pliers, the pliers having a pair of pivoted jaws which press the legs of the clip together. The method can also include a step (iv) of moving the legs closer together in response to shrinkage of the site which would otherwise cause the clip to become loosened; step (iv) being accomplished due to a self-biasing force urging the legs together as a result of the shape memory effect. If the legs have a first length in a longitudinal direction and the clip includes at least one bend in each of the legs when the alloy is in its austenitic state and the legs have a second length in the longitudinal direction without a bend when the alloy is in its martensitic state with the second length being greater than the first length, step (ii) will result in the legs being pressed together without the bend in each of the legs, and step (iii) will result in the corner of the bend in one of the legs being pressed in the longitudinal direction against the inside of the bend in the other leg thereby forming a locking or gripping of the tissue. Alternately, the corners could press together in an opposed fashion to grip the tissue.

BRIEF DESCRIPTION OF THE DRAWING

The invention will now be described with reference to the attached drawing, in which:

FIG. 20b shows a top view of the clip shown in FIG. 20a;

FIG. 22b shows a side view of the clip shown in FIG. 22a; and

DETAILED DESCRIPTION OF THE PREFERRED EMBODIMENTS

The present invention provides an improved surgical fastening clip made of a shape memory alloy. The clip can be applied in the same manner as existing surgical fastening clips, that is, a pliers-like tool can be used to plastically deform the clip over a vessel or tissue of a living person or animal. Surgical fastening clips are typically used to stop bleeding during surgical procedures. However, a problem with existing conventional clips is that they have no ability to continue to exert a clamping force on the vessel or tissue as the vessel or tissue deforms, shrinks, moves, etc. as it responds to the clip and/or thins out as it loses fluid due to compression force. Accordingly, a drawback of existing conventional clips is that they frequently become loose or fall off, allowing bleeding to recur, and the clips may even fall into the surgical zone. The clip according to the invention solves the problem of loosening and/or falling off of conventional clips by using the shape memory effect to generate a continuous constant stress and, hence, constant or increasing pressure through the clip on the tissue or vessel even as the tissue or vessel deforms, shrinks, moves, etc.

Figures 1, 2, 3, 4, 5:
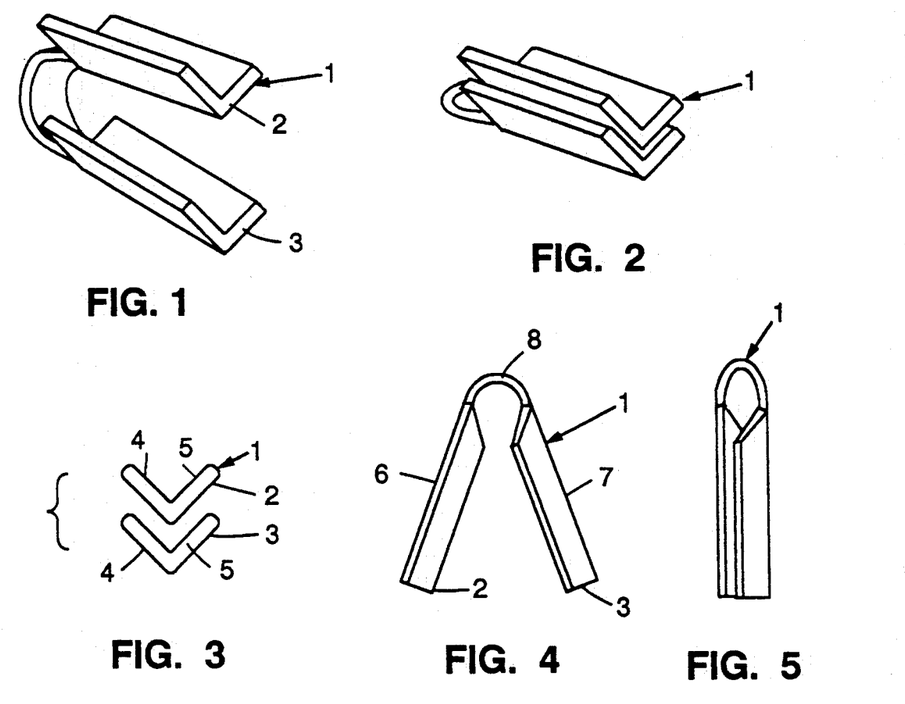
FIG. 1 shows a surgical fastening clip according to the invention in an open configuration.
FIG. 2 shows the clip of FIG. 1 in the closed configuration.
FIG. 3 shows a transverse cross-section of the clip shown in FIG. 2.
FIG. 4 shows a side view of the clip shown in FIG. 1.
FIG. 5 shows a side view of the clip shown in FIG. 2.

One embodiment of the surgical fastening clip, according to the invention, is shown in FIG. 1. In particular, the clip 1 comprises a substantially U-shaped member of a shape memory alloy having a martensite transformation temperature below which the alloy transforms to its martensitic state and an austenite transformation temperature above which the alloy transforms to its austenitic state. The clip is deformable in its martensitic state from the first configuration, such as the closed configuration shown in FIG. 2 to a second configuration, such as the open configuration shown in FIG. 1. The clip recovers the first configuration when heated to transform the alloy to its austenitic state. As shown in FIG. 1, the clip is open and capable of being deformed in its martensitic state so as to apply a first clamping force on an object and so as to apply a second clamping force on the object when the alloy is heated to transform it to its austenitic state, the second clamping force being greater than the first clamping force. That is, when the clip shown in FIG. 1 is deformed in its martensitic state to the configuration shown in FIG. 2, upon heating the clip so as to transform to its austenitic state, the clip which already is in its closed configuration exerts an even greater clamping force since legs 2, 3 of the clip try to move towards each other in the austenitic state.

The alloy selected for the shape memory alloy of the clip in accordance with the invention preferably transforms to its austenitic state at a temperature below 37° C. In accordance with a preferred embodiment of the invention, the alloy transforms to its austenitic state at a temperature in the range of about 32° to 35° C.

The clip of the invention can have various shapes. For instance, the clip can have the shape shown in FIGS. 1-5 wherein each of the legs is substantially V-shaped in lateral cross-section. For instance, each of the legs can include a pair of longitudinally extending sections 4, 5, the sections being joined together at lower longitudinally extending edges thereof and being laterally separated from each other at upper longitudinally extending edges thereof, as shown in FIG. 3.

The clip can comprise a single flat strip of material which has been deformed into the U-shaped member.

Figure 6:
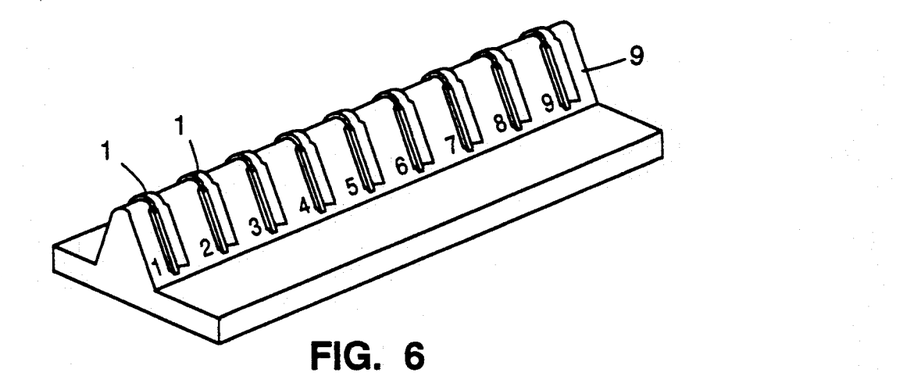
FIG. 6 shows a perspective view of a plurality of clips in accordance with the invention mounted on a rack.

The flat strip of material can include longitudinally spaced-apart end sections 6, 7 forming the legs 2, 3 and a center section 8 therebetween, as shown FIG. 4. The center section 8 has laterally spaced-apart edges which are closer together than laterally spaced-apart edges of each of the end sections 6, 7. As shown in FIGS. 1-3, each of the end sections can include a longitudinally extending V-shaped bend. The clips according to the invention can be packaged, as shown in FIG. 6, wherein a plurality of clips is provided on a suitable support member 9. Multiple clips could be stacked in an application device (not shown) where they would automatically advance one at a time to the open end of the device after the clip ahead is applied.

Figure 7:
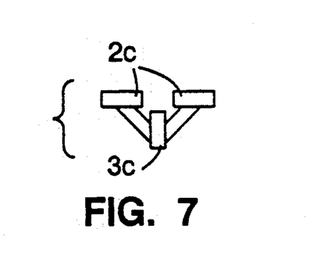
FIGS. 7-9 show alternative shapes for the surgical fastening clip according to the invention.
Figure 8:
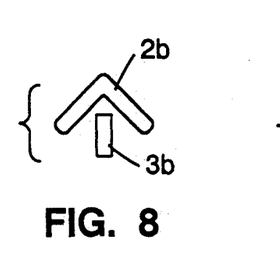
Figure 9:
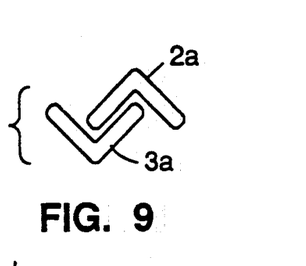

The clip 1 can have shapes other than those shown in FIGS. 1-5 wherein the V-shaped bend on leg 2 includes a pair of upper surfaces which face a pair of lower surfaces of the V-shaped bend on the other leg 3. For instance, the clip shown in FIG. 9 includes V-shaped bends which fit together in a complementary manner such that only one upper surface of the lower V-shaped bend on leg 3a faces one surface of the upper V-shaped bend on leg 2a. Alternatively, as shown in FIG. 8, one of the legs 2b can include a V-shaped bend which is substantially V-shaped in lateral cross-section, and the second leg 3b can be substantially rectilinear in lateral cross-section. In this case, the second leg 3b includes a longitudinally extending edge thereof located intermediate opposed longitudinally extending edges of the first leg 2b. In particular, the first leg 2b includes a concave surface facing the second leg 3b. In another embodiment, the first leg 2c can include two laterally spaced-apart and longitudinally extending portions thereof, as shown in FIG. 7. In this case, the second leg 3c is located intermediate the two portions of the first leg, the two portions of the first leg 2c being flat and coplanar with each other. The second leg 3c can also be flat and lie in a plane which is perpendicular to a plane containing the two portions of the first leg, as shown in FIG. 7.

Figure 10:
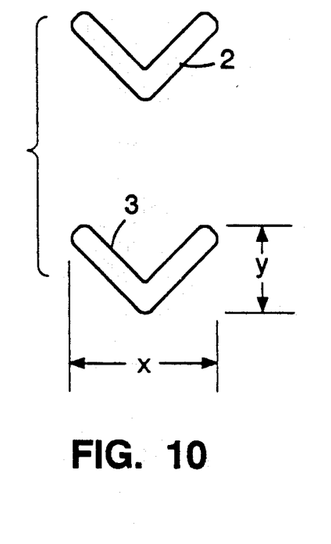
FIGS. 10-12 show various x-y dimensions for the surgical fastening clips in accordance with the invention.
Figure 11:
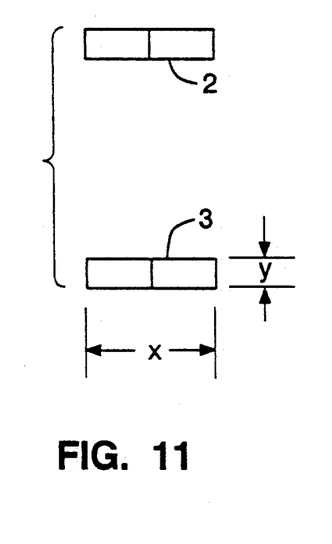
Figure 12:
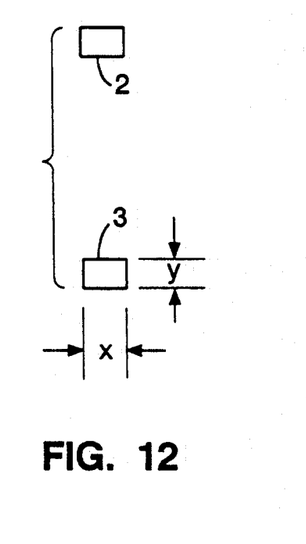

FIGS. 10-13 show end views of inventive clips in their open configuration. FIGS. 10-12 show the relative dimensions of each leg of the clip. The clip shown in FIG. 11 has a smaller "y" dimension than the clip shown in FIG. 10, and the clip shown in FIG. 12 has a smaller "x" dimension than the clip shown in FIG. 11. The clip shown in FIG. 12 with the smaller "x" and "y" dimensions allows the clip to be placed in narrow or tight locations.

FIG. 12 also illustrates how legs of "zig-zag" shape can be mechanically straightened in the martensitic state to reduce the "x" and "y" dimensions—which not only allows the clip to be used in narrow locations—but also provides additional clamping forces in the longitudinal direction when the clip is heated to transform the shape memory alloy into its austenitic state. That is, when the clip shown in FIG. 12 transforms to austenite to its "zig-zag" shape, the bends formed in each leg of the clip not only move toward each other in a transverse direction extending perpendicular to and through the legs, but also move toward each other in a longitudinal direction which is parallel to the legs when the clip is in its closed configuration. This provides clamping forces in the transverse direction and in the longitudinal direction.

Figure 13:
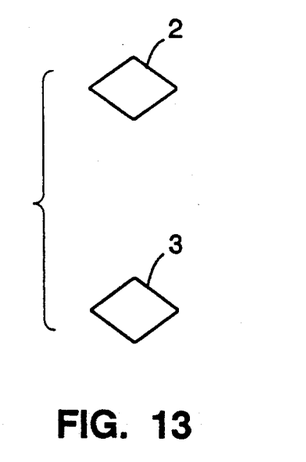
FIG. 13 shows a further embodiment of the surgical fastening clip according to the invention prior to undergoing a shape memory transformation.
Figure 14:
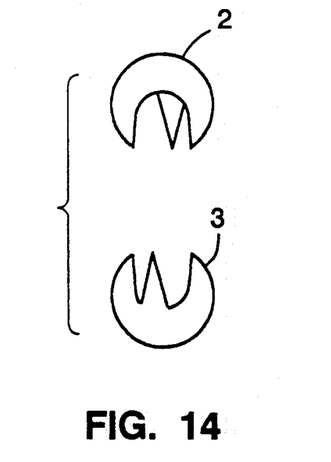
FIG. 14 shows a clip according to the invention after it undergoes a shape memory effect.

FIG. 13 shows a clip according to the invention which is ready to be applied to a suitable site. FIG. 14 shows a clip after it has been applied to a site and undergone a transformation to the austenitic state.

Figure 15:
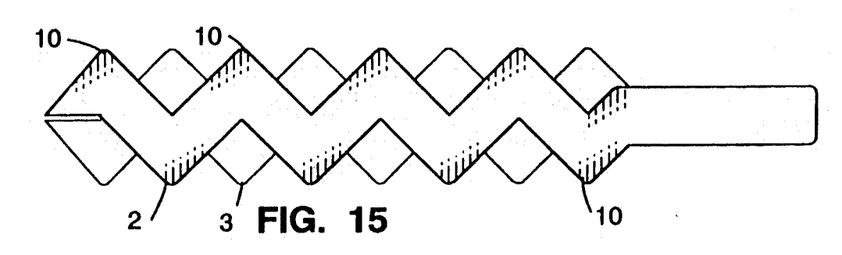
FIG. 15 shows a top view of a surgical fastening clip according to a further embodiment of the invention.
Figure 16:
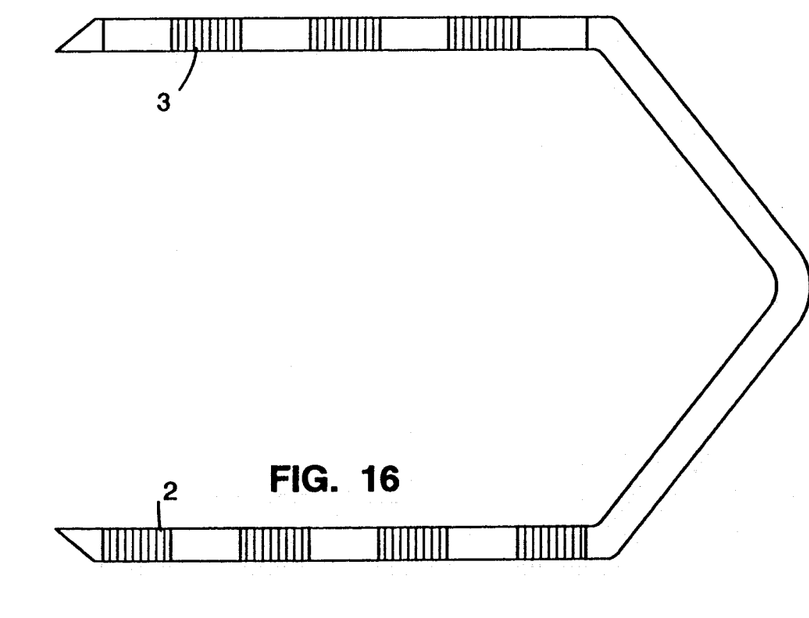
FIG. 16 shows a side view of the clip shown in FIG. 15.
Figure 17:
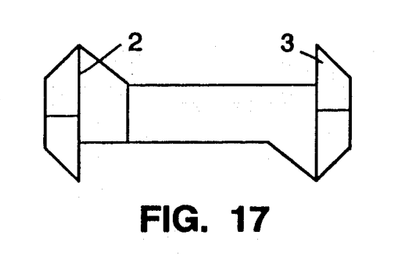
FIG. 17 shows an end view of the clip shown in FIG. 16 in the direction towards the open end of the clip.
Figure 18:
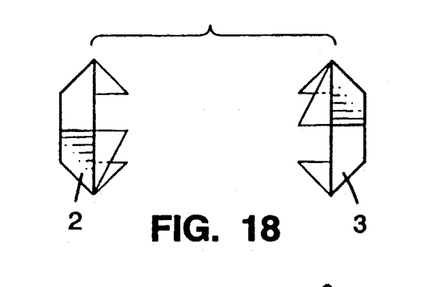
FIG. 18 shows an end view of the clip shown in FIG. 16 in the direction towards the open end of the clip after the clip has undergone a shape memory effect but with the arms separated for clarity of illustration.
Figure 19:
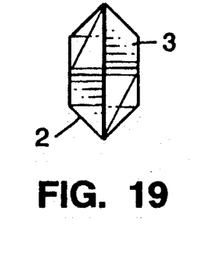
FIG. 19 shows the clip of FIG. 18 in a closed configuration.

As pointed out above, it may be desirable to provide a clamping action in the longitudinal and transverse directions. This can be accomplished by providing the legs of the clip with a "zig-zag" shape. As shown in FIG. 15, each leg can include at least one bend 10 therein. This design will allow the clip to hold the tissue very tightly and to prevent slipping. Further details of the "zig-zag" clip of FIG. 15 are shown in FIGS. 16-19. FIGS. 16 and 17 show the clip in the open configuration. FIG. 18 shows the clip after undergoing a shape memory effect but with the arms separated for clarity of illustration. FIG. 19 shows the clip of FIG. 18 with the legs together in the closed position.

Figures 20A, 20C:
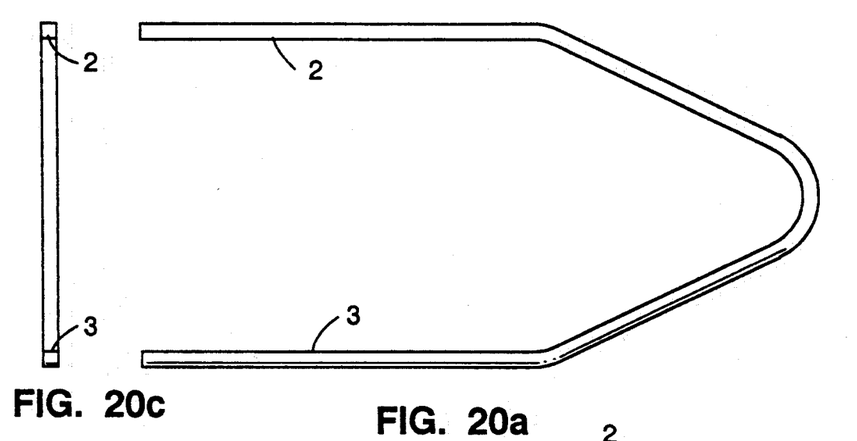
FIG. 20a shows a side view of a zig-zag type surgical fastening clip in accordance with another embodiment of the invention.
FIG. 20c shows an end view of the clip shown in FIG. 20a in the direction towards the open end of the clip.
Figure 20B:
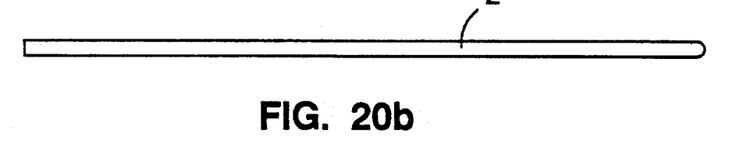
Figures 21A, 21B:
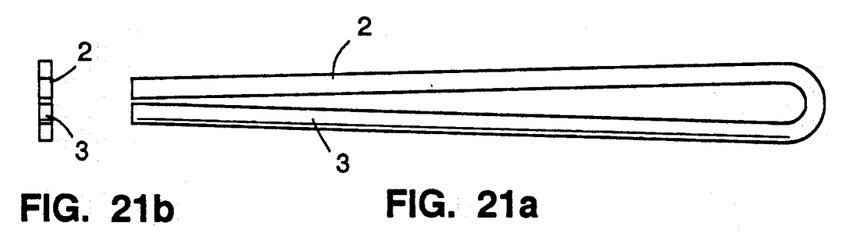
FIG. 21a shows a side view of the clip shown in FIG. 20a after application of the clip but before a shape memory effect takes place.
FIG. 21b shows an end view of the clip shown in FIG. 21a in the direction towards the open end of the clip.
Figure 22A:
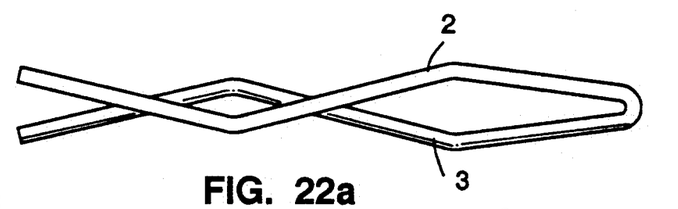
FIG. 22a shows a top view of the clip shown in FIG. 21a after the shape memory effect has taken place.
Figure 22B:
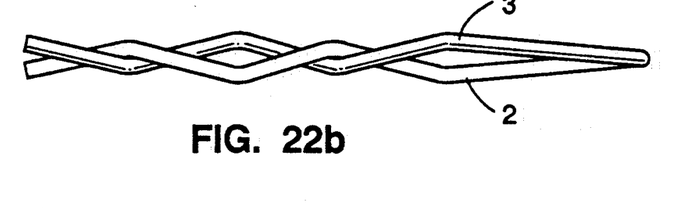
Figure 22C:
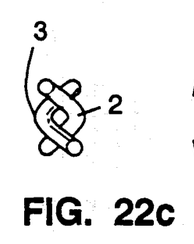
FIG. 22c shows an end view of the clip shown in FIG. 22a in the direction towards the open end of the clip.

FIGS. 20-22 also show details of a "zig-zag" type clip in accordance with the invention. In particular, FIGS. 20a-c show side, top and end views, respectively, of a clip in its open configuration. FIGS. 21a-b show side and end views respectively, of the clip in its applied configuration. In its closed configuration, the clip will have the memorized shape shown in FIGS. 22a-c which show top, side and end views, respectively. After application by squeezing down on a vessel or tissue (in the state shown in FIGS. 21a-b), the clip will rapidly undergo a temperature rise to body temperature causing it to change its shape toward the memorized shape shown in FIGS. 22a-c. This results in about a 10% longitudinal shrinkage of the clip as well as interdigitating teeth or fingers which enhance the tenacious hold of the clip on the tissue and helps prevent it from sliding or slipping off. This quality makes the clip a more dependable and secure surgical fastening device.

The present invention also provides a method for making a surgical fastening clip having a shape memory effect. The clip comprises the shape memory alloy described earlier, and the method comprises a step (i) of providing a shape memory alloy having a martensite transformation temperature below which the alloy transforms to its martensitic state and an austenite transformation temperature above which the alloy transforms to its austenitic state, the alloy being deformable in its martensitic state from a first configuration to a second configuration and recovering to the first configuration when heated to transform the alloy to its austenitic state. A step (ii) is performed by forming the alloy into a clip having a substantially U-shaped configuration with two spaced-apart opposed legs extending in a longitudinal direction. A step (iii) is then performed by deforming the clip such that the opposing legs are squeezed together in a closed configuration. A step (iv) is then performed by heating the clip in the closed configuration such that the alloy transforms to its austenitic state. This is the step in which the memory of the clip is set with the clip in the closed configuration. A step (v) is then performed by cooling the clip such that the alloy transforms to its martensitic state. Then, a step (vi) is performed by deforming the clip such that the legs are moved away from each other from the closed configuration to an open configuration, the clip being open and capable of being deformed in its martensitic state so as to apply a first clamping force on an object and so as to apply a second clamping force on the object when the alloy is heated to transform it to its austenitic state, the second clamping force being greater than the first clamping force. In addition, one or more heat-treating steps can also be applied to the clip for the purposes of forming and heat-treating the clip.

Step (iii) can further include forming at least one projection on at least one of the legs such that when the clip is in its closed configuration the projection extends through a plane extending between the legs. Alternatively, step (iii) can further include forming a plurality of projections on each of the legs such that when the clip is in its closed configuration the projections interengage. In order to provide clamping forces in the longitudinal and transverse directions, step (iii) includes forming each of the legs with at least one bend extending perpendicular to the longitudinal direction, and step (vi) further includes straightening each of the legs such that the legs are elongated in the longitudinal direction. In this case, when the alloy is deformed into its closed configuration and then is heated to transform the alloy to its austenitic state, the legs will attempt to resume to the configuration formed by step (iii). Also, step (iii) can further include forming each of the legs in a "zig-zag" pattern, and step (vi) can further include elongating each of the legs to at least partially remove the zig-zag pattern.

The invention also provides a method of in vitro clamping of living tissue, such as a vessel or passageway in a human or animal, to stop bleeding or to connect the tissues together. In particular, the clamping method includes a step (i) of placing opposing legs of a generally U-shaped surgical fastening clip which is in an open configuration around a site of living tissue. The clip comprises a shape memory alloy having a martensite transformation temperature below which the alloy transforms to its martensitic state and an austenite transformation temperature above which the alloy transforms to its austenitic state. The clip is deformable in its martensitic state from a first configuration to a second configuration and recovers to the first configuration when heated to transform the alloy to its austenitic state. The clip is open and capable of being deformed in its martensitic state so as to apply a first clamping force on an object and so as to apply a second clamping force on the object when the alloy is heated to transform it to its austenitic state, the second clamping force being greater than the first clamping force. The method includes a step (ii) of pressing the legs together to the closed configuration so as to apply the first force to the site. The method includes a step (iii) of heating the clip such that the alloy transforms to its austenitic state and the legs are urged together due to the shape memory effect of the shape memory alloy so as to apply the second force to the site.

The step (ii) is preferably performed at ambient temperature such as in the range of 20° to 25° C. The clip preferably undergoes the shape memory effect by heating in step (iii) to a temperature of less than 37° C., such as a temperature of about 30° to 35° C. Step (ii) can be performed with surgical pliers, the pliers having a pair of pivoted jaws which press the legs of the clip together. A way of applying an electrical current to cause the temperature change of the clip may be used. The method can also include a step (iv) of moving the legs closer together in response to shrinkage of the site which would otherwise cause the clip to become loosened, step (iv) being accomplished due to a self-biasing force urging the legs together as a result of the shape memory effect.

According to a further feature of the invention, the legs can have a first length in a longitudinal direction with at least one bend in each of the legs when the alloy is in its austenitic state, the legs having a second length in a longitudinal direction without a bend therein when the alloy is in its martensitic state such that the second length is greater than the first length. In this case, step (ii) results in the legs being pressed together without the bend in each of the legs, and step (iii) results in shrinkage of the legs in a longitudinal direction such that the bend in one of the legs presses in a longitudinal direction against the bend in the other one of the legs. The shortening of the clip in the longitudinal direction helps to prevent flattening or thinning of the tissue, thereby making it more readily gripped by the clip or the teeth on the clip.

While the invention has been described with reference to the foregoing embodiments, various changes and modifications can be made thereto which fall within the scope of the appended claims.

What is claimed is:

1. A surgical fastening clip, comprising:

a substantially U-shaped member of a shape memory alloy having a martensite transformation temperature below which the alloy transforms to its martensitic state and an austenite transformation temperature above which the alloy transforms to its austenitic state;

the clip being deformable in its martensitic state from a closed configuration to an open configuration and recovering to the closed configuration when heated to transform the alloy to its austenitic state; and the clip being in the open configuration and capable of being deformed to the closed configuration in its martensitic state so as to apply a first clamping force on an object and so as to apply a second clamping force on the object when the alloy is heated to transform it to its austenitic state, the second clamping force being greater than the first clamping force, the clip including first and second opposing legs joined together at one end thereof, the legs having free ends at the other end thereof, the clip including means for applying a clamping force in a longitudinal direction parallel to the first and second legs when the clip is in the closed configuration and the clip transforms to its austenitic state, the clamping force in the longitudinal direction being provided by shrinkage in the longitudinal direction of at least one of the legs of the clip when the clip transforms to its austenitic state.

2. The clip claim 1, wherein the alloy transforms to its austenitic state at a temperature in the range of about 30° to 35° C.

3. The clip of claim 1, wherein the alloy transforms to its austenitic state at a temperature below 37° C.

4. The clip of claim 1, wherein the clip comprises a single flat strip of material which has been deformed into the U-shaped member.

5. The clip of claim 4, wherein the flat strip of material includes longitudinally spaced-apart end sections forming the legs and a center section therebetween, the center section having laterally spaced-apart edges which are closer together than the laterally spaced-apart edges of each of the end sections.

6. The clip of claim 1, wherein the second leg is substantially rectilinear in lateral cross-section.

7. The clip of claim 6, wherein the second leg includes a longitudinally extending edge thereof located intermediate opposing longitudinally extending edges of the first leg.

8. The clip of claim 7, wherein the first leg includes a concave surface facing the second leg.

9. The clip of claim 1, wherein the first leg includes two laterally spaced-apart and longitudinally extending portions thereof.

10. The clip of claim 9 wherein the second leg is located intermediate the two portions of the first leg.

11. The clip of claim 9 wherein the two portions of the first leg are flat and coplanar with each other.

12. The clip of claim 9 wherein the second leg is flat and lies in a plane which is perpendicular to a plane containing the two portions of the first leg.

13. The clip of claim 1 wherein the first and second clamping forces are in a transverse direction which is perpendicular to and extends through the first and second legs.

14. The clip of claim 1 wherein at least one of the first and second legs includes at least one bend perpendicular to the longitudinal direction which is formed when the clip is heated and transforms to its austenitic shape.

15. The clip of claim 1 wherein the first leg has a first length in the longitudinal direction between the ends thereof when the alloy is in its martensitic state and the first leg has a second length in the longitudinal direction between the ends thereof when the alloy is heated and transforms to its austenitic state, the second length being shorter than the first length.

16. The clip of claim 15, wherein the first leg includes a first projection thereon and the second leg includes a second projection thereon, the first and second projections moving toward each other in the longitudinal direction when the alloy transforms to its austenitic state.

17. A method of making a surgical fastening clip having a shape memory effect, comprising:
(i) providing a shape memory alloy having a martensite transformation temperature below which the alloy transforms to its martensitic state and an austenite transformation temperature above which the alloy transforms to its austenitic state, the alloy being deformable in its martensitic state from a closed configuration to an open configuration and recovering to the closed configuration when heated to transform the alloy to its austenitic state;
(ii) forming the alloy into a clip having a substantially U-shaped configuration with two spaced-apart opposing legs extending in a longitudinal direction;
(iii) forming each of the legs with at least one bend along a length thereof;
(iv) deforming the clip such that the opposing legs are squeezed together in a closed configuration;
(v) heating the clip in the closed configuration such that the alloy transforms to its austenitic state;
(vi) cooling the clip such that the alloy transforms to its martensitic state; and
(vii) straightening each of the legs to at least partially remove the bend such that the legs are elongated in said longitudinal direction and deforming the clip such that the legs are moved away from each other from said closed configuration to said open configuration, the clip being open and capable of being deformed in its martensitic state so as to apply a first clamping force on an object and so as to apply a second clamping force on the object when the alloy is heated to transform to its austenitic state, the second clamping force being greater than the first clamping force.

18. The method of claim 17, wherein step (iii) further comprises forming at least one projection on at least one of the legs such that when the clip is in its closed configuration the projection extends through a plane extending between the legs.

19. The method of claim 17, wherein step (iii) further comprises forming a plurality of projections on each of the legs such that when the clip is in its closed configuration the projections interengage.

20. The method of claim 17, wherein step (iii) further comprises forming each of the legs in a zig-zag pattern and step (vii) further comprises elongating each of the legs to at least partially remove the zig-zag pattern.

21. A method of in vitro clamping of living tissue such as a vessel or passageway in a human or animal, comprising:
(i) placing opposed legs of a generally U-shaped surgical fastening clip which is in an open configuration around a site of living tissue, the clip comprising a shape memory alloy having a martensite transformation temperature below which the alloy transforms to its martensitic state and an austenite transformation temperature above which the alloy transforms to its austenitic state;
the clip being deformable in its martensitic state from a closed configuration to an open configuration and recovering to the closed configuration when heated to transform the alloy to its austenitic state;
the clip being open and capable of being deformed in its martensitic state so as to apply a first clamping force on an object and so as to apply a second clamping force on the object when the alloy is heated to transform it to its austenitic state, the second clamping force being greater than the first clamping force;
(ii) pressing the legs together to the closed configuration so as to apply said first force to the site; and
(iii) heating the clip such that the alloy transforms to its austenitic state and the legs are urged together due to the shape memory effect of the shape memory alloy so as to apply said second force to the site.

22. The method of claim 21 wherein step (ii) is performed at ambient temperature.

23. The method of claim 21 wherein step (ii) is performed at a temperature in the range of 20° to 25° C.

24. The method of claim 21 wherein the clip undergoes the shape memory effect by heating in step (iii) to a temperature of less than 37° C.

25. The method of claim 21 wherein the clip undergoes the shape memory effect by heating in step (iii) to a temperature of about 30° to 35° C.

26. The method of claim 21 wherein step (ii) is performed with surgical pliers, the pliers having a pair of pivoted jaws which press the legs of the clip together.

27. The method of claim 21, wherein in step (iii) the legs move closer together in response to shrinkage of the site which would otherwise cause the clip to become loosened, step (iii) being accomplished due to a self-biasing force urging the legs together as a result of the shape memory effect.

28. The method of claim 21 wherein the legs have a first length in a longitudinal direction with at least one bend in each of the legs when the alloy is in its austenitic state, the legs having a second length in the longitudinal direction without a bend therein when the alloy is in its martensitic state with the second length being greater than the first length, step (ii) resulting in the legs being pressed together without the bend in each of the legs and step (iii) resulting in shrinkage of the legs in the longitudinal direction such that the bend in one of the legs presses in the longitudinal direction against the bend in the other one of the legs.

* * * * *